United States Patent [19]

Gabriel et al.

[11] Patent Number: 4,916,317

[45] Date of Patent: Apr. 10, 1990

[54] METHOD AND A DEVICE FOR DETECTING CHANGES IN A SURFACE STATE AND FOR MONITORING THE SURFACE STATE

[75] Inventors: Jean-Marie Gabriel, Le Pecq; Louis Cognet, Le Vesinet; Robert Semet, Lyon; Gilles Courtois; Nadine M. R. Courtois, both of Ecully, all of France

[73] Assignee: Societe Lyonnaise Des Eaux, Paris, France

[21] Appl. No.: 254,360

[22] Filed: Oct. 6, 1988

[30] Foreign Application Priority Data

Oct. 9, 1987 [FR] France ............................... 87 13969

[51] Int. Cl.$^4$ ........................................... G01N 21/55
[52] U.S. Cl. ................................ 250/341; 250/358.1; 356/445
[58] Field of Search .................... 250/341, 340, 358.1, 250/352; 356/445

[56] References Cited

U.S. PATENT DOCUMENTS 4,142,802  3/1979  Pollak et al. ..................... 356/445

OTHER PUBLICATIONS

Tozer, "Developing the Laser Corrosion Monitor", Physics in Technology, 6(6), pp. 251–257, Nov. 1975.

Primary Examiner—Carolyn E. Fields
Attorney, Agent, or Firm—Amster, Rothstein & Ebenstein

[57] ABSTRACT

A method of detecting changes in a surface state and of monitoring said surface state, in particular for a body whose surface is at a given temperature and is in contact with a flowing liquid at a given temperature which may optionally be different from the temperature of said surface, wherein a reference metal body is placed in said liquid, said body having a surface at a temperature which is adjustable independently of the temperature of said liquid, and said body acting as an electrode which is optionally raised to an adjustable potential, and the surface state of said body is detected by measuring the intensity of light radiation reflected from at least one mirror-forming portion of the surface of the reference body.

15 Claims, 3 Drawing Sheets

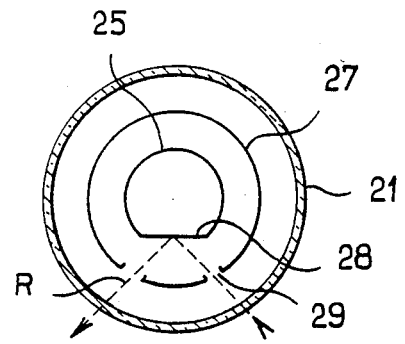
FIG_3c
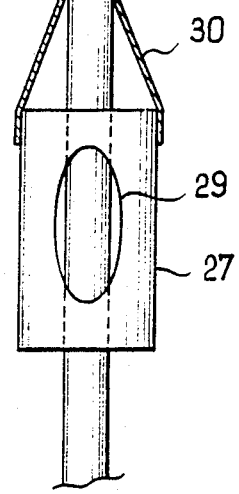
FIG_3b
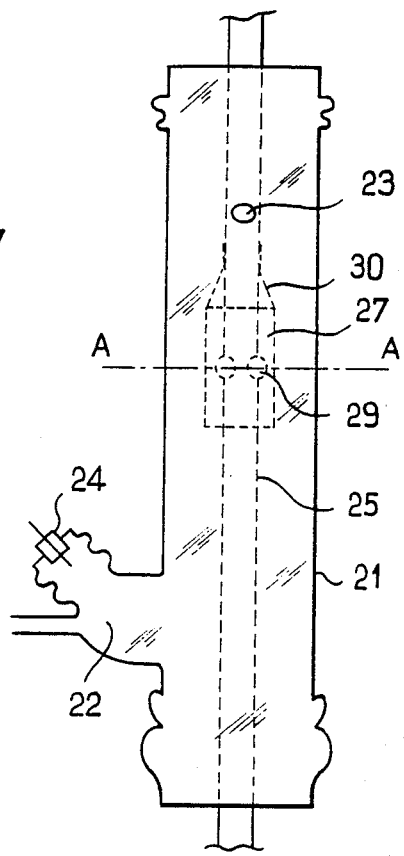
FIG_3a
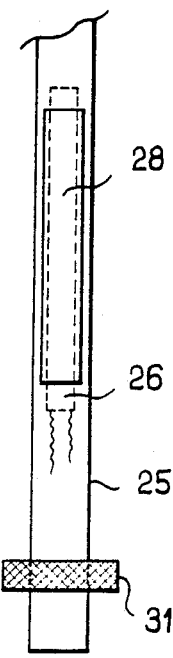
FIG_3d

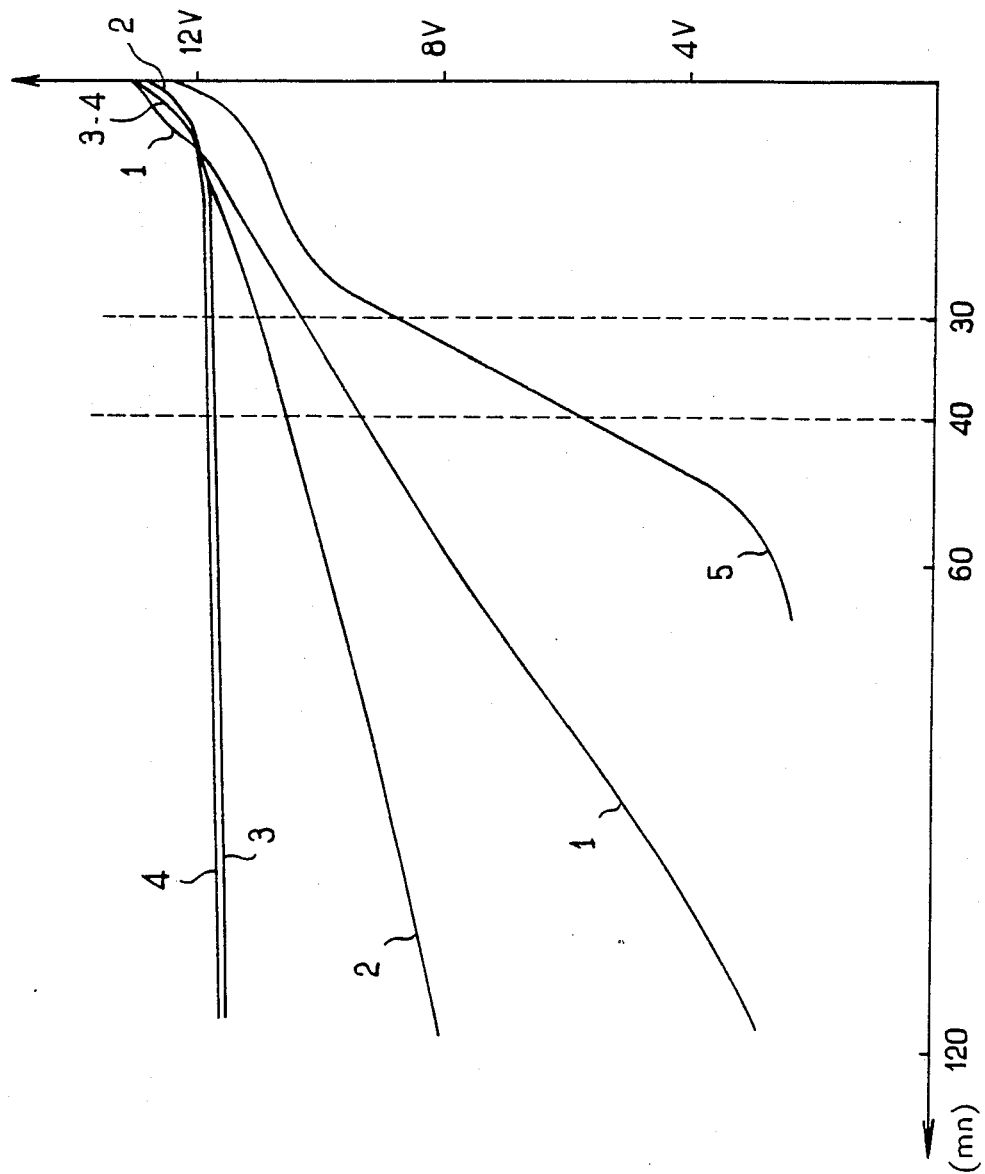
FIG_4

METHOD AND A DEVICE FOR DETECTING CHANGES IN A SURFACE STATE AND FOR MONITORING THE SURFACE STATE

The invention relates to a method and a device for detecting changes in a surface state and for monitoring the surface state, in particular for a surface which is in contact with a liquid flowing in pipework.

BACKGROUND OF THE INVENTION

Deposits occur in pipework in all fields, regardless of whether or not the liquids are water-based. When the liquid is water, specific mention may be made of problems which occur in piping potable water, industrial water, boiler water, cooling water, etc.

Deposits may be formed by calcium carbonate (scale), by metal oxides, by atmospheric dirt in circuits open to the air, by microbes, or by corrosion products. With mixtures or solutions of various substances, other types of deposit may also be encountered (e.g. due to substances precipitating from the solution).

The liquid may also attack the surface of the pipework, and one particular form of corrosion is due to metal, generally iron, being attacked by water since, thermo-dynamically speaking, there is no known domain over which water and iron can remain stably in contact under natural conditions.

These phenomena give rise to considerable drawbacks. Deposits progressively block up pipes, thereby reducing flow rates or increasing head losses, and they also reduce heat exchange capacity, whereas corrosion damages pipework and may lead to breakage.

With natural water, the practical equilibrium between calcium bicarbonate and carbon dioxide is governed by rather complex laws and a shift in the equilibrium position can give rise to chemical reactions in which calcium carbonate is dissolved (aggressiveness) or deposited (scaling), and these reactions may be superposed on the straight-forward electro-chemical corrosion reactions which are specific to metals.

Thermodynamic calculation methods have been developed for attempting to estimate the scaling or corrosive nature of a given water. However, the large number of such methods (Tillmans' method, Langeliers's method, Hoover'diagram, Hallopeau's method, Franquin and Marceaux's diagram, . . . ) is witness to the difficulty of this approach. These methods are based on studying pure solutions under determined conditions of pH, temperature, and concentration, and they are not capable of taking account of the complexity of practical situations. In addition, the results of such calculations are often of the YES/NO type as to the possibility of precipitation taking place, without giving any possibility of investigating the kinetics of the phenomena.

In order to mitigate these drawbacks, methods and apparatuses have been developed for using the water of the circuit concerned to obtain a representation (which may be accelerated) of these phenomena so as to be able to correct them and possibly prevent them from taking place.

A first method consists in placing thermocouples in a special circuit off the main circuit and in measuring variations in the heat exchange coefficient. This method gives an indication of the state of the apparatus without requiring direct inspection, e.g. in the cooling circuits of electricity power supply stations. This method thus does not make it possible to forecast scaling but only to observe it, and then only providing that the same conditions are maintained in the special circuit as in the main circuit, in particular with reference to temperature. This method is lengthy in application since the phenomenon takes place under real operating conditions and since cleaning the special circuit after it has been scaled turns out to be difficult.

Another method makes use of measuring variation in current flow obtained by applying a constant potential (of about $-1$ V relative to a saturated calomel reference electrode). Recording current variation provides information on the scaling of the electrode constituted by the metal under investigation. The apparatus containing the metal sample, the reference electrode, and the auxiliary electrode in water taken from the main circuit is itself placed in a thermostatically controlled bath. This method has the advantage over the preceding method of making it possible to forecast scaling, e.g. over a period of three hours at 40° C. However, it suffers from the drawback that sensitivity cannot be changed without changing either the temperature or the imposed potential, since the same means are being used both for giving rise to scaling and for measuring it.

Further, since it is the bath itself which is heated or otherwise, rather than the metal sample, conditions on the surface of the sample are, by virtue of this very fact, very different from reality, in particular when considering heat exchangers. This means that the deposit is generally constituted by the calcite form of calcium carbonate, whereas in reality the aragonite form is obtained or else an association of both forms, depending on the temperature of the surface on which the deposit takes place.

Similar problems occur with phenomena of deposition or corrosion in the presence of liquids other than natural water.

In order to mitigate these drawbacks, the present invention seeks to provide a device enabling the conditions of the phenomenon to be created using parameters which are adjustable so as to reproduce the operating characteristics of the real circuit, or to create characteristics which accelerate the phenomenon, by using means for detecting the phenomenon and measuring variations therein, which means are separate from the means used for setting up experimental conditions.

SUMMARY OF THE INVENTION

The present invention thus provides a method of detecting changes in a surface state and of monitoring said surface state, in particular for a body whose surface is at a given temperature and is in contact with a flowing liquid at a given temperature which may optionally be different from the temperature of said surface, wherein a reference metal body is placed in said liquid, said body having a surface at a temperature which is adjustable independently of the temperature of said liquid, and said body acting as an electrode which is optionally raised to an adjustable potential, and the surface state of said body is detected by measuring the intensity of light radiation reflected from at least one mirror-forming portion of the surface of the reference body.

By putting the surface of the reference body at the desired temperature, either merely by allowing the body to take up the temperature of its environment or else by heating the body to obtain a desired temperature at its surface, it is possible to track the phenomenon under normal conditions, and if the surface of the reference body is subjected to additional heating and/or to the application of a potential, then the phenomenon is accelerated, thereby making forecasting possible.

Detection by measuring the intensity of radiation, e.g. infrared radiation, as reflected from at least one mirror-forming portion of the surface is completely independent from the means for setting up the phenomenon to be detected, and as a result the conditions under which the phenomenon appears can be changed without interferring with the conditions under which it is observed.

The invention also provides a device for implementing the method, the device comprising a cell having a liquid inlet, a liquid outlet, two electrodes connected to a potentiostat, with one of said two electrodes being constituted by the reference body, and also a reference electrode, with at least a portion of the surface of the reference body constituting a mirror, with the reference body including heating means, and with the device further including an emitter-receiver of light radiation disposed in such a manner as to emit a light beam towards the mirror and receive the light beam reflected by the mirror.

In a particular embodiment of the cell, the reference body is constituted by a hollow tube including a flat which serves as the mirror, and the heating means are constituted by a heating plug placed inside the tube.

The method may be applied to monitoring the surface state of pipework by placing the device either directly in a main network or else by placing it in a secondary network which reproduces the conditions of a main network, with the phenomenon being accelerated or otherwise. The method and the device may also be used for performing studies on natural liquids or on synthetic liquids.

The observed surface of the reference body is a surface on which a phenomenon occurs which is quantatively and qualitatively similar to the phenomenon which actually takes place in the pipework. It may be constituted by a surface whose composition is the same as that of the real surface, or which is slightly different so long as it behaves in the same way. However, account must be taken of the fact that since the observed surface is initially polished so as to be reflective, the phenomenon may be initiated differently.

In another embodiment of the cell, the portion serving as the mirror is a flat removable portion.

BRIEF DESCRIPTION OF THE DRAWINGS

Implementations and embodiments of the invention are described by way of example with reference to the accompanying drawings, in which:

FIGS. 3a to 3d are views showing the main parts of the device shown in FIG. 2; and FIG. 4 is a graph as a function of time showing the fall in the measured voltage which is itself a function of the reflected intensity, for various mixtures of water having different concentrations of calcium carbonate.

MORE DETAILED DESCRIPTION

Figure 1:
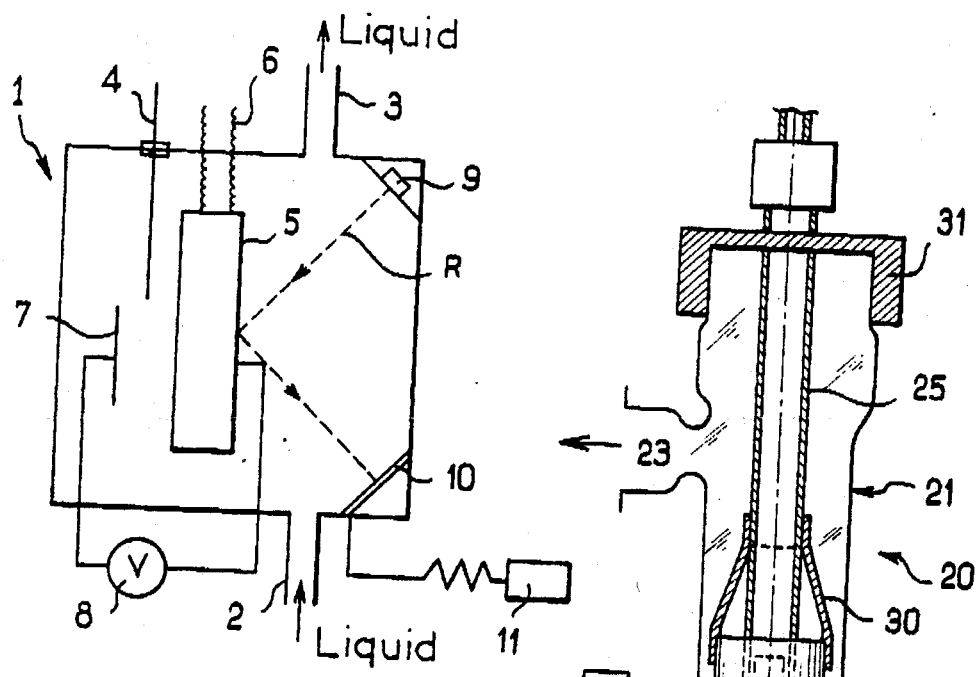
FIG. 1 is a theoretical diagram for explaining operation of a device in accordance with the invention.

The detection and monitoring cell 1 as shown diagrammatically in FIG. 1 includes a liquid inlet orifice 2 and a liquid outlet orifice 3. A reference electrode 4 is placed inside the cell. A main electrode or body 5 fitted with heating means 6 is mounted inside the cell 1 together with an auxiliary electrode 7. The electrodes 5 and 7 are connected to corresponding terminals of a potentiostat 8, with the electrode 5 being a cathode or an anode. An emitter 9 of light radiation R is positioned at a certain angle (e.g. 45°) relative to the electrode 5, and a receiver 10 is placed in such a manner as to receive the radiation reflected by the electrode 5. This receiver (a photodiode) is coupled to a resistance, and the voltage across the terminals of the resistance is measured, with variations in the voltage being displayed or recorded at 11 and being representative of changes in the surface state of the electrode 5.

The cell operates as follows: the liquid is caused to flow through the cell 1 at a determined flow rate; the surface of the electrode is brought to the desired temperature either by merely allowing thermal equilibrium to be established between the main electrode 5 and the liquid, or else by heating the electrode 5 using the heater means 6 until it reaches a temperature corresponding either to the temperature of the inside skin of the pipework (independently of the temperature of the liquid itself, e.g. in a heat exchanger), or else to a higher temperature in order to accelerate the phenomenon.

The surface state of the main electrode then changes because of the deposition phenomenon and/or the corrosion phenomenon which is to be monitored.

A light beam or ray R, e.g. of infrared light, is emitted by the emitter 9 and travels towards the portion of the electrode 5 which constitutes a mirror at which it is reflected towards the receiver or photodiode 10. The formation of a deposit or of corrosion on the mirror-forming surface reduces the intensity of the reflected light beam and as a result the voltage provided by the readout device 11 is observed to diminish as a function of time.

In this case, although the method serves to monitor the appearance of the phenomenon, it also serves, unlike the prior art, to reproduce the real phenomenon. This is particularly advantageous for scaling where the relative proportions of the calcite and aragonite forms of calcium carbonate vary, inter alia, as a function of the temperature of formation.

In a particularly advantageous application of the method, after the electrode 5 has achieved the desired temperature, it is set back to a desired potential. To do this, a reference electrode 4 is included in the cell and a constant potential relative to the reference electrode 4 is applied to the electrodes (the cathode 5 and the auxiliary electrode 7, or vice versa) by means of the potentiostat. This application of a constant potential accelerates the phenomenon being investigated and thus makes it possible to determine its reaction kinetics and to predict how the phenomenon will evolve as a function of time.

FIGS. 2 and 3a to 3d show a particular embodiment of a device for implementing the theoretical diagram of FIG. 1.

This device is specifically designed for investigating scaling, but it could be used for studying phenomena other than scaling, if necessary with the aid of simple modifications, in particular, to take account, of the physico-chemical characteristics of the liquids being investigated. However, the description of this device is, for reasons of simplicity and clarity, restricted to a device for use with scaling.

Figure 2:
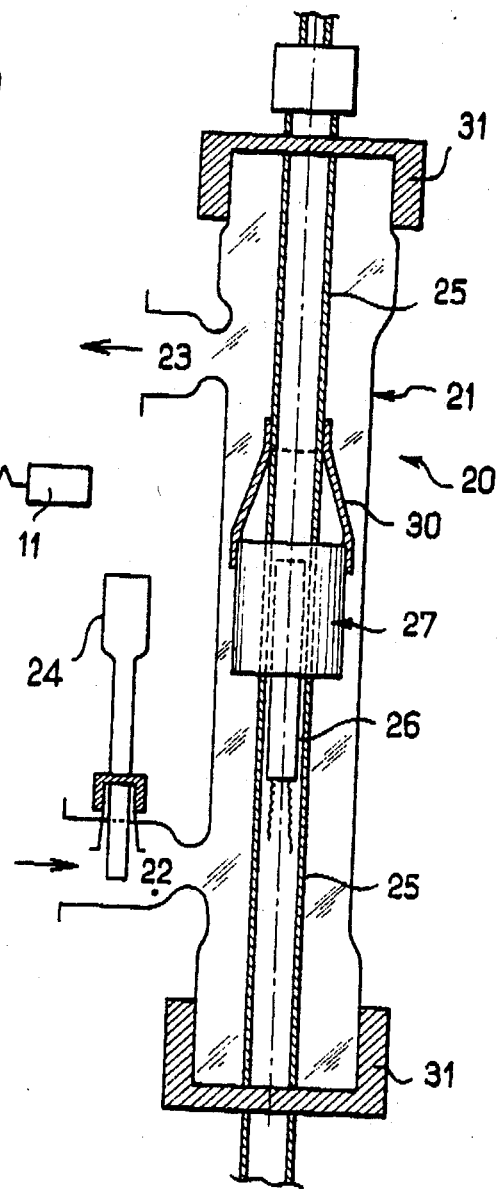
FIG. 2 is a section through a particular embodiment of a device in accordance with the invention.

FIG. 2 is an overall view of a scaling cell 20. It is constituted by a generally cylindrical glass body 21 (where glass is inert relative to water and to the electrolysis reaction), which is disposed vertically and closed at its two ends by respective plugs. The body 21 includes a water inlet orifice 22 and a water outlet orifice 23 with the flow through the body being driven, for example, by a peristaltic pump (not shown). A reference electrode 24 is fitted to the duct leading to the orifice 22. It is preferable to use a simple and stable saturated calomel electrode, but it would also be possible to make use of any other type of reference electrode (e.g. a platinum wire). The main electrode 25 is constituted by a hollow tube, e.g. of stainless steel, which is fixed inside the cell 20 or which passes lengthwise through the cell and through the plugs in order to make disassembly possible. For scaling it acts as a cathode, whereas for investigating corrosion it would act as an anode. In the description of a scaling cell, the main electrode is referred to as the cathode and the auxiliary electrode as the anode. A heating plug 26 is received in the hollow cathode and it is connected to a suitable adjustable source of heating energy (not shown). The anode 27 is a length of hollow tube having a greater diameter than the cathode and placed around the cathode. The plug 26 and the anode are placed in the middle region of the cell 20 in order to facilitate positioning the emitter-receiver of light radiation. The anode 27 is supported from above by a support device 30 which may be frustoconical as shown in the drawing, but which may naturally be of any other appropriate shape or structure. The anode and the cathode are connected in conventional manner to a potentiostat (not shown) which serves to apply a determined constant potential relative to the reference electrode 24. In a scaling cell, it is advantageous to make use of a potential of $-1.060$ V relative to the saturated calomel electrode. Naturally, the selected value will depend on the liquid passing through the cell and on the extent to which it is desired to accelerate the phenomenon under investigation.

A conventional emitter-receiver (not shown) is positioned outside the cell 20 such that the light radiation R (see FIG. 3c) emitted therefrom strikes the cathode 25. In order to enable the incident beam or ray to be reflected, at least a portion of the cathode 25 constitutes a mirror. This may be a flat 28 formed along the entire length of the cathode-constituting tube, or merely on the middle portion thereof, or on any other appropriate section. It may also be a reflecting pellet placed removably in a tube which is metal or otherwise. The utility of such a removable pellet is described below.

By way of example, the emitter may be an infrared emitter powered at 7 V and placed at 45° relative to the reflecting surface, and the receiver of the reflected light beam may be a photodiode driven at 15 V and also positioned at 45° relative to the mirror-forming surface 28 of the cathode 25.

In order to enable the light beam to travel to the mirror, it is necessary to provide openings through the anode which are appropriately disposed relative to the positioning of the emitter-receiver and which allow the light rays to pass through the anode. For example, two openings may be provided which are spaced apart by 90°, either in a horizontal plane if the light beam travels in the horizontal plane, or else in a vertical plane if the light beam travels in a vertical plane. It would also be possible to provide a single elongate opening extending over more than 90° (and more generally over twice the angle of incidence of the light beam). FIG. 3b shows, by way of example, a vertically elongate opening 29, whereas FIGS. 3a and 3c show two openings spaced apart at 90° in a horizontal plane.

In another possible embodiment of the device, the light beam may be transmitted to the vicinity of the mirror-forming surface by means of optical fibers. The fibers pass through the body 21 in sealed manner, and also though the anode, if necessary. The angle of incidence is selected as desired, and may even by 90° if the optical fibers are coaxial with each other.

It is particularly advantageous to use optical fibers for conveying the light radiation when the water under investigation, or more generally the liquid under investigation, is highly colored or very turbid which has the effect of absorbing a portion of the emitted light prior to its reflection on the mirror and of spoiling the measurement results. However, this drawback may be mitigated by using an emitter-receiver system having two beams (a measuring beam and a reference beam) if optical fiber apparatus is not available.

The following example is given to illustrate operation of the device.

EXAMPLE

Apparatus similar to that described above and shown in FIG. 2 was used under the following operating conditions to perform tests on five different water mixtures obtained by mixing natural water with deionized water in proportions given in the following table.

OPERATING CONDITIONS

Reference electrode 24: saturated calomel electrode; electrode potential: 1.080 V relative to the electrode 24;

flow rate (adjustable between 9 and 20 ml/min): 9 ml/min;

temperature obtained using a 100 W/220 V plug 26: 70° C.;

IR emitter: feed voltage 7 V—adjusted to 940 nm;
receiver: photodiode driven at 15 V; and
angle of incidence: 45°.

| Mixture No. | Natural Water | Deionized Water | Concentration of $Ca^{++}$ and $HCO_3^-$ in meq/l |
|---|---|---|---|
| 1 | 100% | 0% | 5 |
| 2 | 75% | 25% | 4 |
| 3 | 50% | 50% | 2.5 |
| 4 | 25% | 75% | 1.25 |
| 5 | 100% | 0% | 10 |

+additional $CaCO_3$

The curves shown on the graph of FIG. 4 were obtained, where each curve is referenced by the number of the corresponding water mixture in the table.

It can be seen for low concentrations of calcium carbonate (mixtures No. 3 and 4), that after a short period during which deposition takes place, the curves tend towards horizontal straight lines. There is no further change in the surface state, and scaling is thus no longer taking place. In contrast, at higher concentrations, the transmitted light intensity continues to diminish. However, it may be observed that after a certain length of time, on the order of 30 minutes, the curves have portions which are substantially linear. This characteristic makes it possible to define a time interval, e.g. of 10 minutes duration situated between 30 minutes and 40 minutes, over which the slopes of the curves may be measured in order to obtain an indication of the scaling power of the water by calculating a suitable index.

When the apparatus is used for monitoring purposes (without applying a potential thereto) this index makes it possible, in particular, to detect any abnormal variation in the scaling power and thus to trigger an alarm or act on appropriate compensating devices either automatically or manually. To this end, the reading and/or recording apparatus 11 may be connected to a calculation unit which, if it determines that the slope of the voltage curve is greater than a predetermined value, provides an output signal which may trigger an alarm, for example.

When the device is used for studying water prior to its being used in a real installation, results can be obtained rapidly by applying a potential to the device, for example making it possible to predict behavior, e.g. after a period of 3 hours at 40° C., whereas in conventional experimental models, studies require up to fifteen days.

Further, the electrode can easily be cleaned and at the same time the thickness of the deposit can be calculated, thereby making it possible to discover its effect on heat exchange, in particular.

To this end, after the device has operated for a desired length of time, e.g. 40 minutes, for ensuring that deposition takes place and for measuring the slope of the voltage curve, heating is turned off and the electrolysis current is reversed and fixed at a value of 10 mA.

This causes the following anode reaction to take place:

$$2H_2O \rightarrow O_2 + 4H^+ + 4e^-$$

The pH at the electrode drops and the protons formed redissolve the previously-deposited fur in accordance with the following reaction:

$$CaCO_3 + H^+ \rightarrow HCO_3^- + Ca^{++}$$

The reflecting surface is thus cleaned progressively, and the cleaning is completed when the measured voltage returns to its initial value.

Since electrolysis has taken place at constant current, Faraday's law may be applied and the mass of calcium carbonate dissolved can consequently be calculated from the time required for redissolving it.

Given the density of $CaCO_3$, it is possible to calculate the thickness of the fur that had been formed.

Further, since it is possible to vary the temperature of the reflecting surface independently both of the other formation parameters and of the detection system, it is possible to study the crystal forms of the deposit formed as a function of temperature and to verify that the calcite form, the aragonite form or a combination of those forms is obtained depending on the applied temperature.

To this end, it may be desirable to provide a removable reflecting surface which can be removed from the apparatus prior to cleaning in order to examine the deposit formed thereon by other techniques such as electron microscopy, infrared spectrometry, etc. If the removable reflecting surface is a pellet, the deposit formed thereon will also be in the form of a pellet and may be directly analyzed in an infrared spectrometer.

The above description of a particular embodiment of the device for a particular application (scaling) has naturally been given purely by way of example, and it is obvious that the invention has numerous applications both for monitoring purposes and for forecasting and investigation in all fields where phenomena may occur which change the state of a surface which is in contact with a liquid.

We claim:

1. A method of detecting changes in and monitoring the surface state of a reference body of metal whose surface is at a given temperature and is in contact with a flowing liquid at a given temperature, which may optionally be different from the given temperature of the surface, comprising the steps of placing the reference body in the liquid, the reference body having a surface at a temperature which is adjustable independently of the temperature of the liquid, and the reference body acting as an electrode which is optionally raised to an adjustable potential, and detecting the surface state of the reference body by measuring the intensity of light radiation reflected from at least one mirror-forming portion of the surface of the reference body.

2. A method according to claim 1, wherein the surface of the reference body is heated to a selected temperature which is kept constant, and changes in the surface state of the reference body are then detected as a function of time.

3. A method according to claim 1, wherein the surface of the reference body is left at ambient temperature and the changes to which the surface is subjected are detected as a function of time.

4. A method according to claim 1, wherein, after putting the surface of the reference body at a desired temperature, the reference body acting as an electrode is raised to a potential which accelerates changes in its surface state, and changes in its surface state are detected as a function of time.

5. A method according to claim 1, wherein the light radiation is infrared radiation.

6. A method according to claim 1, wherein the liquid is water and the changes in the surface state are due to scaling.

7. A device for use with an emitter of light radiation and a receiver of light radiation for detecting changes in and monitoring the surface state of a reference body of metal whose surface is at a given temperature and is in contact with a flowing liquid at a given temperature, which may optionally be different from the given temperature of the surface; the device comprising a cell having a liquid inlet orifice and a liquid outlet orifice, a potentiostat, two electrodes connected to said potentiostat, one of said two electrodes being constituted by the reference body, said reference body including heating means, and at least a portion of the surface of said reference body constituting a mirror, said mirror comprising means for receiving a light beam from the emitter of light radiation and serving to reflect the radiation to the light radiation receiver.

8. A device according to claim 7, wherein the reference body is constituted by a hollow tube including a flat serving as the mirror and wherein the heating means are constituted by a heating plug placed inside the tube.

9. A device according to claim 7, wherein said portion of the surface constituting the mirror is disposed on a removable flat portion of the reference body.

10. A device according to claim 7, additionally including the emitter and the receiver, and wherein the emitter is an emitter of infrared radiation and the receiver is constituted by a photodiode coupled to a resistance and wherein means are provided for measuring the voltage across the terminals of the resistance.

11. A device according to claim 10, wherein the emitter and the receiver are positioned at 45° relative to the mirror.

12. The device according to claim 7 configured and dimensional so as to comprise means for monitoring scaling.

13. A device according to claim 7 additionally including a third electrode acting as a reference electrode for the two electrodes.

14. A device according to claim 13 configured and dimensioned so as to comprise means for monitoring scaling.

15. A device according to claim 7 additionally including the emitter and the receiver.

* * * * *